United States Patent [19]

Teeple

[11] Patent Number: 4,661,096
[45] Date of Patent: Apr. 28, 1987

[54] ANTI-AIR EMBOLISM AND ANTIBLOOD LOSS DEVICE FOR CVP CATHETER

[76] Inventor: Edward Teeple, 641 Ridgefield Ave., Mt. Lebanon, Pa. 15216

[21] Appl. No.: 773,876

[22] Filed: Sep. 6, 1985

[51] Int. Cl.⁴ .............................................. A61M 5/00
[52] U.S. Cl. .................................. 604/122; 604/249; 604/256; 137/599
[58] Field of Search ................................ 604/122–124, 604/236, 245–247, 249, 256, 30, 31, 33; 137/599

[56] References Cited

U.S. PATENT DOCUMENTS

| | | | |
|---|---|---|---|
| 2,392,045 | 1/1946 | Hudgins | 604/247 |
| 3,176,690 | 4/1965 | H'Doubler | 604/174 |
| 3,441,249 | 4/1969 | Aslan | 137/599 X |
| 3,559,678 | 2/1971 | Donner | 137/599 X |
| 4,324,239 | 4/1982 | Gordon et al. | 604/249 X |
| 4,535,819 | 8/1985 | Atkinson et al. | 604/122 X |
| 4,568,333 | 2/1986 | Sawyer et al. | 604/122 |

Primary Examiner—Stephen C. Pellegrino
Attorney, Agent, or Firm—Reed Smith Shaw & McClay

[57] ABSTRACT

An anti-air embolism device for use between a patient's CVP catheter and source of fluid comprising inlet connection mean adapted to connect said device with a source of fluid; an outlet means including means for locking said device to the patient's CVP catheter; a passageway connecting said inlet and outlet connection means for fluid passage, and an occluder interposed within said passageway to prevent the entrainment of air within the patient's CVP catheter upon disconnection of a source of fluid at said inlet connection means.

6 Claims, 2 Drawing Figures

ANTI-AIR EMBOLISM AND ANTIBLOOD LOSS DEVICE FOR CVP CATHETER

FIELD OF THE INVENTION

The present invention relates to a device to protect against air embolisms and blood loss due to disconnections between intravenous fluid lines and patient connected to such lines.

BACKGROUND OF THE INVENTION

The present invention overcomes the serious problems associated with the unintentional disconnection of a patient from an intravenous fluid line. Patients who become disoriented or restless may inadvertently cause a CVP (central venous pressure) catheter to disconnect from the fluid line. This problem can also occur during diagnostic work-ups, or during ambulation or the like. In such accidental disconnects, it is possible for air to enter and become entrained in the catheter giving rise to the possibility of an air embolism or for the loss of blood if there is a positive pressure CVP. There is little risk to the patient if the disconnect is witnessed early and corrected, but if it is not, the foregoing problems can arise and lead to morbidity or mortality.

While these problems have been known in the art, no means has been devised to economically solve them. Numerous valves and other means exist to prevent fluid back flow in CVP catheters and other intravenous fluid lines. An example of these is disclosed in U.S. Pat. No. 4,324,239. These devices are all useful for their intended purposes, but do not obviate the need for a means of protecting the patient from an accidental disconnect.

Accordingly, it is an object of the present invention to provide an economical means for preventing the formation of an air embolism caused by the entrainment of air in a CVP catheter due to the accidental loss of connection. It is a further object of the invention to provide a device which is easily and inexpensively manufactured so as to be disposable and yet prevent such air embolisms and the loss of blood. It is not, however, the purpose of this invention to provide a device which prevents an air embolism caused by air being placed under pressure in the CVP line; other devices in the art are available to prevent such disasters.

SUMMARY OF THE INVENTION

Generally, the present invention provides an anti-air embolism device for use between a patient's CVP catheter and source of fluid comprising an inlet connection mean adapted to connect the device with a source of fluid and an outlet means including means for locking the device to the patient's CVP catheter. The device also includes a passageway connecting said inlet and outlet connection means for fluid passage, and an occluder interposed within said passageway to prevent the entrainment of air within the patient's CVP upon disconnection of a source of fluid at said inlet connection means.

In the preferred embodiment of the invention, a second passageway is provided between the inlet and outlet means which bypasses the first occluder. The second passageway includes a second occluder means which is manually actuatable to permit continuous monitoring by a physician of the CVP. However, when not needed for such monitoring the occluder is biased to restrict the flow of fluid.

Other advantages of the invention will become apparent from a perusal of the following detailed description of a presently preferred embodiment taken in connection with the accompanying drawing.

PREFERRED EMBODIMENT OF INVENTION

Figure 1:
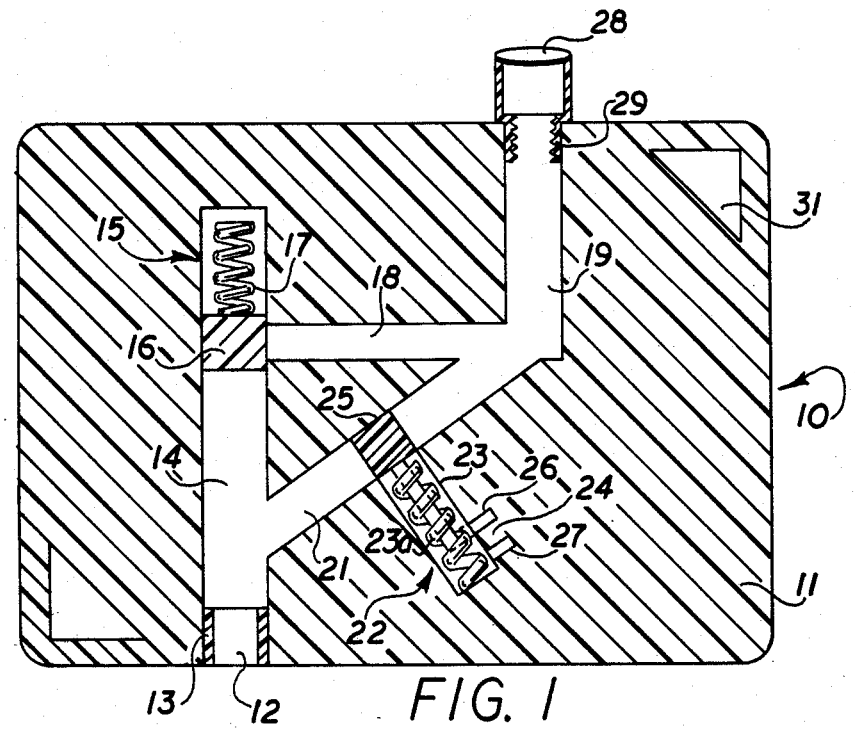
FIG. 1 is a diagrammatic view of the present invention showing the general arrangement of parts.
Figure 2:
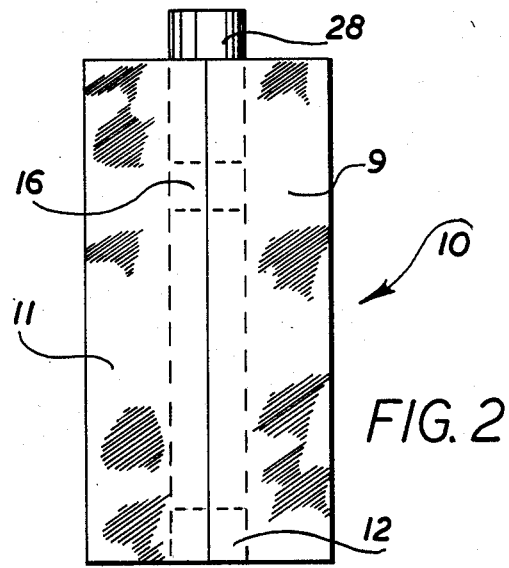
FIG. 2 is a left side elevation of the present invention.

Referring to the drawing, the anti-air embolism device 10 of the present invention comprises two molded complementary halves which are glued or otherwise cemented or welded together. Preferably, device 10 is about one inch square or rectangular and molded from polyethylene or the like material. Shown in the drawing is first half 11, but it is to be understood the description of the invention will be with respect to the entire device 10 and that complimentary portions of the second half 9 of device 10 are implicit.

Along one edge of device 10 is an opening 12 which is adapted to connect to a fluid line (not shown) from a bag of fluid (IV solution) or a CVP monitoring device. Around the periphery of opening 12 is an integral female connector 13 to facilitate connection to such lines. The female connector 13 is designed to be the "weak" connection between the fluid/monitoring lines and the patient; that is, if a disconnect is to occur it is designed to occur at this connection. As will be described hereinafter, device 10 is designed to be secured to the patient to interpose the required safety. With prior art CVP connectors this is the point where, if a disconnect occurs, air would be entrained within the CVP catheter or, if positive back pressure existed, a potentially fatal blood loss would occur.

Opening 12 defines the entrance to passageway 14 which permits the passage of fluid to the patient. Positioned at the end of passageway 14 is occluder 15, preferably having a square cross section. Occluder 15 includes a valve 16 adapted to move within the occluder and prevent the flow of fluids passed the valve when seated against the end of passageway 18. Valve 16 is biased into passageway 14 by means of spring 17. Preferably, spring 17 permits (retracts) for the flow of fluids when the pressure of the fluid within passageway 14 is greater than 2 cm $H_2O$.

In fluid connection with occluder 15 is passageway 18 which permits the fluid entering passageway 14 under pressure to bypass occluder 15 and on to the patient. Preferably, passageways 18 and 14 are of a round cross section with 18 having a diameter less than dimension of occluder 15 to facilitate the sealing of the respective passageways by valve 16. As shown in the drawing, passageway 18 is connected to passageway 19 to provide a fluid exit from device 10 to the patient. It is to be understood however that passageways 18 and 19 may be conveniently made as a single passage.

At the intersection of passageways 18 and 19 is an opening connecting directly with passageway 14 by means of monitoring channel 21. Monitoring channel 21 permits the continuous monitoring of the CVP if that is desired by the attending physician. Provided in channel 21 is flow control occluder 22 having a valve 25 which prevents the flow of fluid through channel 21. Valve 25 is operably connected to control shaft 23 and spring biasing means 23a. If the physician desires to monitor the central venous pressure, valve 25 is manually opened against the spring bias by pulling on tab 26 which is mounted on to shaft 23 and positioned into slot 27 located at the end of the occluder channel. The retraction of shaft 23 and with its locking in slot 27 opens channel 21 to fluid flow and CVP monitoring.

Locking means 28 is mounted to device 10 preferably by screwing into threaded end 29 of passageway 19. Locking means 28 locks the patient's CVP to device 10. To further prevent separation or disconnection, openings 31 are provided in device 10 so that it may be stitched to the skin of the patient. The locking means 28 is designed to be the strong link in connection between the source of fluid and the patient so that any accidental disconnection will occur at opening 12. If such disconnection occurs, it can be seen that the immediate loss of fluid pressure in passage 14 will result in occluder 15 closing passage preventing air from becoming entrained in the patient's CVP. Likewise it will prevent the flow of blood from the patient.

While one embodiment of the present invention has been described in particularity, it may be otherwise embodied within the scope of the appended claims.

What is claimed is:

1. An anti-air embolism safety device adapted for placement between a central venous pressure (CVP) catheter which is attached to a patient and an external source of intravenous fluid being infused into the patient, comprising:
   (a) a formed body adapted to operably connect the catheter and the external fluid source;
   (b) an inlet connection means within the body adapted to operably connect with said fluid source;
   (c) a fluid outlet means on the body and further comprising means for locking the outlet means to the catheter;
   (d) a first passageway within the body communicating between the inlet and the outlet means and adapted for intravenous fluid passage therethough;
   (e) a first occluder means interposed within the first passageway biased to prevent the entrainment of air therein, and of any airflow to the catheter secured to the outlet means upon the accidental cessation of fluid passage into said inlet means; and
   (f) further wherein (i) a second passageway is provided in said body connecting the inlet and outlet sections of the first passageway so as to bypass the first occluder means and (ii) having a second occluder means normally inserted into said second passageway and being associated with (iii) a linear biasing means that normally interposes the second means into said second passageway to occlude same and (iii) manually operable position adjusting means pinned to the biasing means, adapted for exerting a counterforce against the normal passageway occluding position of said second means sufficient to retract same from said second passageway.

2. The device of claim 1 wherein the second occluder means and associated biasing means are adapted to operate in either of two positions, the first being with the open second passageway, whereby central venous pressure may be read during a non-intravenous flow stage, when the first occluder means will move to occlude the first passageway, whereupon the second passageway is temporarily connectable to a pressure monitoring device; and in the alternate position, with the second occluder means being closed, whereby it precludes air entrainment and patient blood loss upon spontaneous disconnection of the source of intravenous fluid into the inlet means.

3. The device of claim 1 wherein the first occluder means includes a first valve position normally adapted for preventing flow of a fluid passing under pressure through the first passageway by a valve-associated linear biasing means that automatically occludes said first passageway when there is insufficient positive pressure from intravenous fluid flow entering said inlet connection means.

4. A device according to claim 1 wherein the body comprises a formed plastic material of construction suitable for disposal after single use.

5. A device according to claim 1 wherein the body is provided with one or more apertures in nonoperational areas adapted for suturing the device to the body of the patient carrying same, whereby accidental removal of a catheter from a patient is precluded.

6. A device according to claim 1 wherein the first fluid inlet means is adapted to retain an interruptable, pressure-fitted connection means to the fluid supply source and the outlet means is adapted to support securely a means for locking same to the patient catheter, whereby in the event of a spontaneous disconnection of the safety device, the flow rupture occurs only at the inlet means, thus assuring the first occluding means always becomes operative in preventing airflow into the first passageway and any possible entrainment into the downstream catheter.

* * * * *